US005750570A

United States Patent [19]
Voorhees et al.

[11] Patent Number: 5,750,570
[45] Date of Patent: May 12, 1998

[54] METHOD OF TREATMENT OF HYPERPIGMENTATION IN BLACK SKIN WITH RETINOIC ACID AND METHOD OF LIGHTENING BLACK SKIN WITH RETINOIC ACID

[75] Inventors: John J. Voorhees; Charles N. Ellis; Christopher E. M. Griffiths, all of Ann Harbor, Mich.

[73] Assignee: The Regents of the University of Michigan, Ann Arbor, Mich.

[21] Appl. No.: 861,133

[22] Filed: Mar. 31, 1992

[51] Int. Cl.[6] .......................... A61K 31/19; A61K 31/07; A61K 7/44
[52] U.S. Cl. ..................... 514/557; 424/59; 514/725
[58] Field of Search ..................... 424/59; 514/725, 514/557

[56] References Cited

U.S. PATENT DOCUMENTS 5,266,307 11/1993 Voorhees et al. ..................... 424/59

OTHER PUBLICATIONS

Abstract of French Patent 2, 383, 663, Nov. 1978 Nemet.
Mills, Journal. Soc. Cosmet Chem. 1978, vol. 29(3) pp. 147–154 (Biosis Abstract).
Sakamoto et al, Jap. Pat. 02142714, May 31, 1990 (Chem. Abs, 1990, vol. 114(4): 29940q).
Nagashima et al, Jap. Pat. 02028105, Jan. 30, 1990 (Chem. Abs., 1990, vol. 113(4): 29129m.
Kilgman, (Chem. Abs. 1976(18):103773c) German Pat. No. 2,131, 441, Feb. 10, 1972.
Engasser et al, Cosmetics and Dermatology, 1981, Abstract, vol. 5(2), pp. 143–147.
Kilgman, Journal American Academy of Dermatology, 1989, vol. 2113 II Suppl. (650–654).
Fitzpatrick et al, Dermatology in General Medicine, Fitzpatrick et al, eds., vol. 1, McGraw Hill, Inc., New York, pp. 1056–1061 (1993).
Andrews'Diseases of the Skin Clinical Dermatology, Eighth Edition, Arnold et al, eds., W.B. Saunders Co., Philadelphia, p. 809 (1990).
Rook/Wilkinson/Ebling Textbook of Dermatology, vol. 2, Champion et al., eds. Oxford, London, pp. 1527–1528 (5th Edition, 1992).
Robins, Biological Perspectives on Human Pigmentation, pp. 128 (1991).
Rook/Wilkinson/Ebling Textbook of Dermatology, vol. 3, Champion et al, eds., Oxford, London p. 1593 (5th Edition, 1992).
Montagna et al Black Skin Structure and Function, p. 112 (1993).
McDonald, Progress in Dermatology, vol. 7, pp. 15–16 (1973).
Kligman et al, Arch. Dermatol., vol. 111, pp. 40–48 (1975).
Findlay et al, Br. J. Dermatol., vol. 93, pp. 613–622 (1975).
Hoshaw et al. Arch. Dermatol., vol. 121, pp. 105–108 (1985).
Dermatologic Clinics, vol. 6, pp. 275–276 (1988) Grimes et al.

Primary Examiner—Shelley A. Dodson
Attorney, Agent, or Firm—Hopgood, Calimafde, Kalil & Judlowe LLP

[57] ABSTRACT

Hyperpigmentation of black skin may be treated by topical application of retinoic acid to the skin. Topical application of retinoic acid is also effective for lightening normal black skin.

11 Claims, 3 Drawing Sheets

METHOD OF TREATMENT OF HYPERPIGMENTATION IN BLACK SKIN WITH RETINOIC ACID AND METHOD OF LIGHTENING BLACK SKIN WITH RETINOIC ACID

BACKGROUND OF THE INVENTION

1. Field of the Invention

The present method relates to a method of treating hyperpigmentation in black skin with retinoic acid and a method of lightening black skin with retinoic acid.

2. Discussion of the Background

Post inflammatory hyperpigmentation (PIH) presents as irregular, darkly pigmented spots occurring after inflammatory injury to the skin such as from acne, folliculitis, eczema and shaving. PIH resolves slowly but may persist for months. Black subjects of all ages are commonly afflicted with PIH, and the consequent disfigurement may necessitate medical attention (Kenney, Jr. J. A. et al, *Clinics in Dermatology*, 1989; 7:1–10; Grimes P. E. et al, *Dermatologic Clinics*, 1988; 6:271–81; and McDonald C. J. et al, *Progress in Dermatology*, 1979; 4:15–20). Unfortunately, although the biology of skin pigmentation is well understood, therapy of PIH is unsatisfactory, and currently available therapies such as hydroquinones can be associated with unsightly depigmentation, irritant dermatitis and ochronosis (McDonald C. J., *Progress in Dermatology*, 1973; 4:15–20; Kligman A. M. et al, *Arch. Dermatol.*, 1975; 111:40–48; Findlay G. H. et al, *Br. J. Dermatol.*, 1975; 93:613–22; and Hoshaw R. A. et al, *Arch. Dermatol.*, 1985; 121:105–8).

In recent studies of topical retinoic acid (RA) treatment of photodamage, lightening of sun-induced dyspigmentation, i.e., actinic lentigines, has been observed (Weiss J. S. et al, *JAMA*, 1988, 259:527–32; Kligman A. M. et al, *J. Am. Acad. Dermatol.*, 1986; 15:836–59; Weinstein G. D. et al, *Arch. Dermatol.*, 1991; 127:659–65; Rafal E. S. et al, *New Engl. J. Med.*, 1992; 326:368–374; Ellis C. N. et al, *J. Am. Acad. Dermatol.*, 1990; 23:629–37; and Olsen E. A. et al, *J. Am. Acad. Dermatol.*, 1992; 26:215–24). Sun-induced dyspigmentation is a heterogeneous entity in whites (Rafal E. S. et al, *New Engl. J. Med.*, 1992, 326:368–374) which may share features of melanin deposition with PIH. RA has not been previously used for PIH, because it is thought to cause hyperpigmentation and to be poorly tolerated (McDonald C. J. et al, *Progress in Dermatology*, 1973; 4:15–20). Topical RA treatment has also been reported as effective for the treatement of liver spots associated with photodamage (Rafal E. S. et al, *New Engl. J. Med.*, 1992; 326:368–74).

Thus, there remains a need for a method for treating hyperpigmentation. In addition, a method of lightening black skin would also be desirable.

SUMMARY OF THE INVENTION

Accordingly, it is one object of the present invention to provide a method for treating hyperpigmentation in black skin.

It is another object of the present invention to provide a method for treating PIH in black skin.

It is another object of the present invention to provide a method for lightening black skin.

These and other objects, which will become apparent during the following detailed description, have been achieved by the inventors' discovery that retinoic acid is an effective agent for treating hyperpigmentation in black skin and for lightening black skin.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
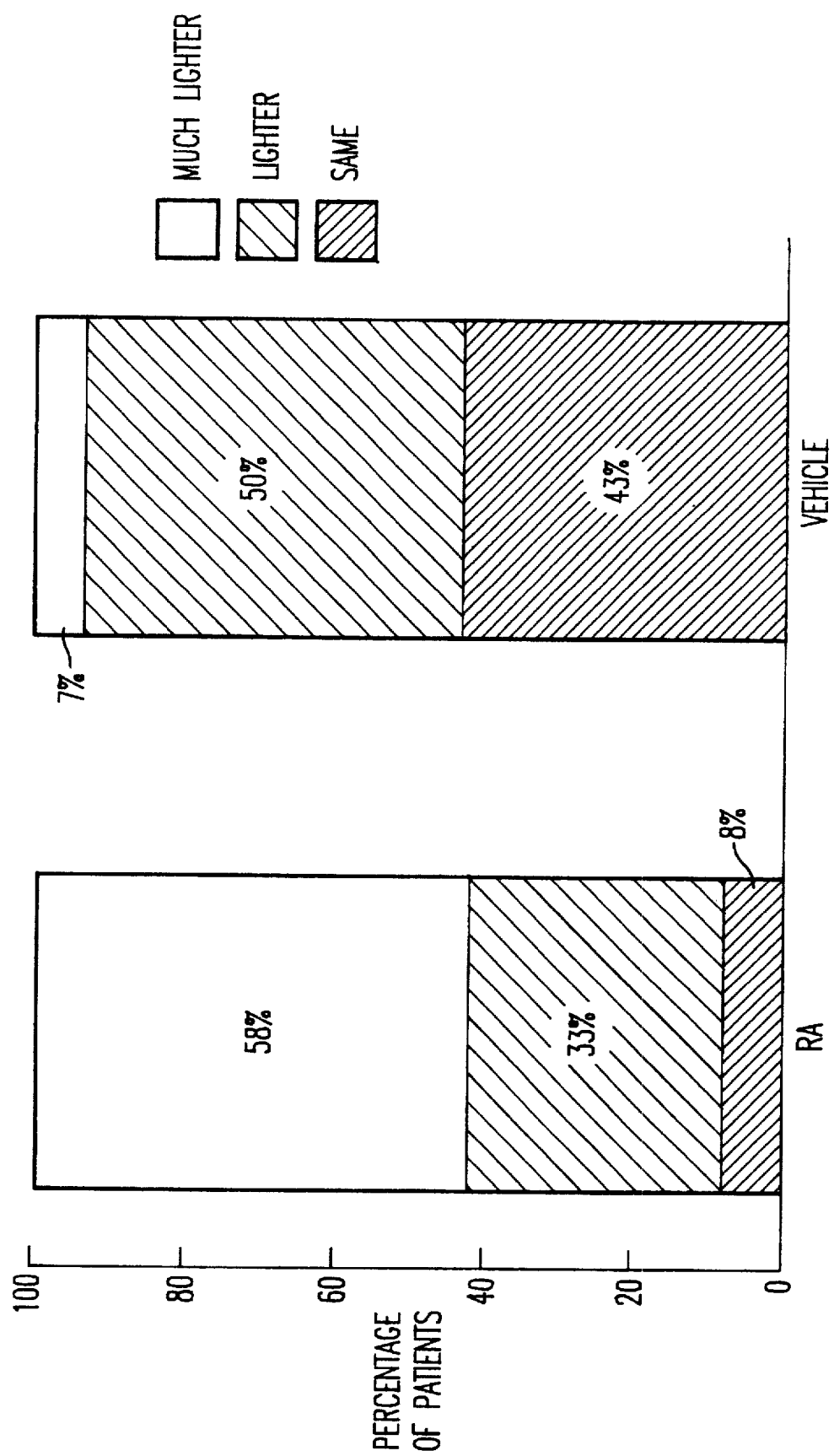
FIG. 1 compares the overall efficacy of 40 weeks treatment with 0.1% RA or vehicle cream for post-inflammatory hyperpigmentation of the face. As compared with vehicle, 0.1% RA cream produced significant improvement ($p<0.0001$)

Thus, in a first embodiment, the present invention relates to a method of treating hyperpigmentation in black skin with retinoic acid. Retinoic acid is a known compound having the formula:

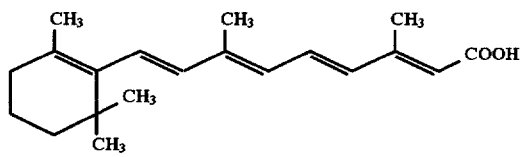

The preparation of retinoic acid is described in U.S. Pat. No. 3,006,939, and Lakshmanan et al, *Biochem. J.*, vol. 90, p. 569 (1964), and the structure has been confirmed by x-ray crystallography by Stam et al, *Acta Cryst.*, vol. 16, p. 62 (1963), all of which are incorporated herein by reference. The properties of retinoic acid are reviewed in Dowling et al, *Vitam. Horm.*, vol. 18, p. 515 (1960), incorporated herein by reference.

In the present method of treating hyperpigmentation of black skin, the retinoic acid is administered by applying a composition containing the retinoic acid directly to the skin to be treated. The composition, which will be described below, is suitably applied in an amount such that the retinoic acid is applied to the skin in an amount of 0.5 to 10 mg/cm$^2$ of skin, preferably 1 to 5 mg/cm$^2$ of skin.

The application of the retinoic acid composition to the skin is preferably carried out in a repetitive fashion. Thus, it is preferred that the composition be applied from 3 to 7 times per week, more preferably 7 times per week. Especially good results have been obtained when the retinoic acid composition is applied to the skin on a daily basis. It is particularly preferred that the composition be applied in the evening, immediately after the skin has been washed and then dried.

The repeated application of the retinoic acid containing composition is suitably carried out over a period of time sufficient to result in an amelioration of the hyperpigmentation. Thus, the treatment is typically carried out for a time of 4 to 40 weeks, more typically 4 to 20 weeks.

It may be advantageous, when carrying out the treatment over a period of weeks or months, to start the treatment with an initial dosage of 0.05 to 1 mg/cm$^2$ of skin, preferably 0.1 to 0.5 mg/cm$^2$ of skin, and then gradually increase the dosage to 0.5 to 10 mg/cm$^2$ of skin, preferably 1 to 5 mg/cm$^2$ of skin as the patient becomes acclimated to the treatment. If, during the treatment, the patient develops any irritation due to the retinoic acid, it may be advantageous to discontinue the treatment for 1 to 4 days, preferably 1 to 2 days, or until the irritation subsides.

As noted, above, the retinoic acid is suitably applied to the skin in the form of a composition. The only requirement with regard to the concentration of the retinoic acid in the composition is that the retinoic acid must be present in an amount such that the desired rate of application of retinoic acid may be achieved by convenient application of the composition to the skin. Thus, the concentration of retinoic acid in the composition is suitably 0.025 to 0.2 wt. %, preferably 0.05 to 0.1 wt. %, most preferably about 0.1 wt. % based on the total weight of the composition.

The composition may take any form which is suitable for application to human skin. Thus, the composition may be in the form of an oil, ointment, cream, lotion, gel, etc. The composition may contain, as additional ingredients, water, oil, alcohols (such as ethanol, isopropanol, or propanol), emulsifying agents, perfumes, coloring agents, fillers, abrasive agents, moisturizers, etc. Especially good results have been obtained using 0.1% Retin-A® Cream (Product of Ortho Pharmaceutical Corp., Raritan, N.J.).

The present method of treating hyperpigmentation is especially effective for treating PIH of black skin.

In a second embodiment, the present invention relates to a method of lightening black skin with retinoic acid. Again, the retinoic acid may be applied directly to the skin to be lightened in the form of a composition. The same compositions used for the treatment of hyperpigmentation may be used for the lightening of black skin. In general, the method of lightening black skin may be carried out as described above for the method of treating hyperpigmentation. However, in this case it may be desirable to continue the treatment for longer periods of time, e.g., 20 to 40 weeks.

The efficacy of retinoic acid for treating hyperpigmentation of black skin and for lightening black skin has now been demonstrated by clinical studies. The present data demonstrate the short term tolerability and efficacy of a retinoic acid composition, such as a 0.1 wt. % cream (0.1% RA) for the treatment of hyperpigmentation, in particular PIH, in black skin. Clinically significant lightening of PIH lesions occurred with use of 0.1% RA, and side effects occurred in fewer subjects (53%) than reported in Caucasians (88%) (Weiss J. S. et al, JAMA, 1988; 259:527-37; and Rafel E. S. et al, New Engl. J. Med., 1992, 326:368-374). Contrary to prior reports (McDonald C. J. et al, Progress in Dermatology, 1973; 4:15-20), topically applied 0.1% RA cream did not result in excessive hyperpigmentation or unwanted depigmentation of the skin in any of the studied patients.

Topically applied RA has been reported to lighten hyperpigmented lesions, i.e., actinic dyspigmentation and nevi in Caucasian skin (Weiss J. S. et al. JAMA, 1988, 259:527-32; Kligman A. M. et al, J. Am. Acad. Dermatol., 1986; 15:836-59; Weinstein G. D. et al, Arch. Dermatol., 1991; 127:659-65; Rafal E. S. et al, New Engl. J. Med., 1992; 326:368-374; Ellis C. N. et al, J. Am. Acad. Dermatol., 1990; 23:629-37; Olsen E. A. et al, J. Am. Acad. Dermatol., 1992; 26:215-24); Edwards L. et al, Arch. Dermatol., 1990; 126, 494-9; and Meyskens F. L., Jr. et al, J. Am. Acad. Dermatol., 1986; 15:822-5). In the present study, 22 of 24 patients (92%) in the RA-treated group demonstrated clinically significant improvement after 40 weeks of treatment. However, 17 of 30 patients (51%) on vehicle therapy also demonstrated lightening of PIH lesions at week 40. This is probably either due to subjects employing a daily skin care regimen, which included sunscreen, or more importantly spontaneous fading of PIH lesions which is known to occur after several months. It is most notable that there was significantly earlier clinical improvement in RA (4 weeks) as compared to vehicle-treated patients (24 weeks). This result is considered to be of practical relevance in that improvement can be expected as early as 4 weeks in some patients (38%).

The results obtained with a colorimeter demonstrate significant lightening of designated PIH lesions and normal skin by RA therapy in comparison with vehicle treatment. This finding has not been reported previously, and although the underlying mechanism of action is unknown. Orlow has reported that RA will inhibit tyrosinase which has already been induced to higher levels (Orlow S. J. et al, J. Invest. Dermatol., 1990; 94:461-4). Indeed, in normal black skin tyrosinase might be considered to be genetically induced and thus capable of inhibition by RA (Iwata M. et al, J. Invest. Dermatol., 1990; 95:9-15).

This histologic data demonstrated no significant decrease in microscopic epidermal melanin in PIH lesions treated with RA despite significant clinical lightening. This is surprising because using the same technology as described herein, the same dermatopathologist (LJF) detected significant reduction in epidermal melanin in liver spots which were clinically lightened by RA. (Rafal E. S. et al, New Engl. J. Med., 1992, 326; 368-374). However, the statistically insignificant decrease in epidermal melanin observed in normal black skin was consistent with the clinical observation of subtle lightening.

Furthermore, Table II shows significant and typical retinoid effects (compaction and increased granular layer) demonstrating pharmacological activity of retinoic acid in the same specimens which exhibited minimal changes in melanin content. It appears that clinically observable differences in skin color can occur in the presence of changes in epidermal melanin content which are essentially undetectable by light microscopy.

A source of potential bias in the present study is the retinoid reaction experienced by some patients. This possibility, although real, is mitigated by the fact that the reaction was seen in only half of the patients treated with RA. Furthermore, clinical improvement and side effects were graded in reference to pretherapy throughout the study, without reference to data from previous visits, thus reducing potential bias. Moreover, the colorimeter, an instrument without bias, provided statistically significant corroboration of the lightening observed in both PIH and normal skin.

In conclusion, the present study demonstrates that topically applied RA is an effective treatment for black patients with PIH with a side-effect profile similar to or less than that seen in Caucasian skin (Weiss J. S. et al, JAMA, 1988, 259:527–32; Kligman A. M. et al, J. Am. Acad. Dermatol., 1986; 15:836–59; Weinstein G. D. et al, Arch. Dermatol., 1991; 127:659–65; Rafal E. S. et al, New Engl. J. Med., 1992; 326:368–374; Ellis C. N. et al, J. Am. Acad. Dermatol., 1990; 23:629–37; and Olsen E. A. et al, J. Am. Acad. Dermatol., 1992; 26:215–24). Topically applied RA is not used to treat PIH in black skin due to insufficient experience and reports of unwanted hyperpigmentation, depigmentation and intolerance (McDonald C. J., Progress in Dermatology, 1973; 4:15–20). The present data demonstrate that normal black skin is not excessively depigmented nor hyperpigmented but is subtly lightened following RA therapy and that PIH lesions are lightened toward the color of normal black skin.

Other features of the invention will become apparent in the course of the following descriptions of exemplary embodiments which are given for illustration of the invention and are not intended to be limiting thereof.

EXAMPLES

METHODS

Patients

Sixty-eight, healthy black patients (21 men, 47 women) with moderate to severe PIH lesions on the face and/or arms were enrolled into the 40 week study. The sample size was chosen to provide statistical power of approximately 0.90 in detecting a difference in overall improvement of at least one-half unit between the two groups at a type I error rate of 0.05 using a two-tailed hypothesis. By use of a computer-generated code, subjects were randomly assigned to receive either RA or vehicle. Thirty-three subjects received RA (9 men, 24 women) and 35 vehicle (12 men, 23 women). The age range was 21–58 years, mean 35 years for the RA treatment group and 20–55 years, mean 34 years for subjects treated with vehicle. Exclusion criteria included medical conditions or concurrent therapy that would interfere with the evaluation of treatment sites. Patients were not to have used topical or systemic retinoids for six months and one year respectively. Topical medications (including hydroquinone or corticosteroid preparations) or systemic steroids were not used for at least two weeks and one month, respectively prior to the study. Pregnant and nursing women, as well as patients with a history of keloids were excluded.

A pertinent medical history and signed informed consent was obtained from all subjects enrolled. Prior to entering the study potential side effects were carefully explained to each patient. The protocol was approved by the University of Michigan Medical Center Institutional Review Board.

Treatment 0.1% RA cream (Retin-A® Cream) and vehicle cream were manufactured and supplied by Ortho Pharmaceutical Corp., Raritan, N.J. Both test creams were packaged and dispensed in identical tubes, such that neither investigators nor patients knew the tube contents or to which treatment group the patient was assigned. Patients applied test cream once nightly to the entire face and/or arms depending on the site of PIH lesions for forty weeks. Patients were initially instructed to apply a pea-size volume of cream and to gradually increase the amount of cream applied to tolerance.

All participants were provided a mild soap or cleansing agent and instructed to wash the test sites twenty minutes prior to applying the test cream. A sunscreen of SPF 15 was also provided and worn during the day. Patients were instructed to avoid exposure to strong sunlight, excessive wind or cold and to minimize cosmetic use. Cosmetics were not worn during evaluations or photographic sessions. Subjects were warned that erythema, stinging, pruritus, and desquamation could result from the treatment and were asked to report these side effects. If side effects were experienced patients temporarily discontinued treatment for a day or two and used moisturizers supplied.

Clinical Evaluations

Evaluations were performed at pretherapy, weeks 2 and 4 and then monthly for 10 months. For determination of efficacy of 0.1% RA versus vehicle an overall evaluation of clinical response of treated areas (face and/or arms) was performed at each return visit and initially graded by the investigator on a scale of 1 to 5 (1=much darker, 5=much lighter) and later reassigned the following −2 to +2 scale (−2=much darker; −1=darker; 0=no change; 1=lighter; 2=much lighter) so that a rating of no change would equal zero.

A separate evaluation of four designated facial and/or upper extremity PIH lesions as well as normal skin was performed on each patient. These four individual PIH lesions were selected as baseline based on ability to accurately locate them throughout the investigation. The designated lesions were representative of other lesions in the same patient and were used to correlate pre and post therapy clinical and histologic results. At each follow-up visit changes in pigmentation of designated lesions and changes in color of normal skin on one cheek as compared with pretreatment were graded on a scale of 1 to 8 (1=much darker, 8=absent) and later reassigned a scale of −3 to 4 (−3=much darker, −2=darker, −1=slightly darker, 0=no change, 1=slightly lighter, 2=lighter, 3=much lighter and 4=absent) as explained above.

Colorimeter

As an objective measure of skin color of four designated individual PIH lesions and normal skin, a colorimeter (Chroma Meter-CR 200b, Minolta Camera Co. Ltd., Osaka, Japan) was used prior to therapy and at weeks 12, 24, and 40. Colorimetric assessment of skin lightening or darkening is a measure of reflectance which is designated by the L value of the L, a, b color system as defined by the Commission International del'Eclairage (Serup J. et al, Clinical and Experimental Dermatology, 1990; 15:267–72). Five colorimeter measurements of each site and normal skin were performed at the above visits and the final measures are given as a mean of these five values.

Safety

Safety was evaluated as severity of erythema, desquamation, burning/stinging and pruritus on face or arms and noted at all visits. A scale of 0 to 4 (0=absent and 4=most severe) was used for these evaluations. Other adverse experiences, new illnesses, changes in systemic or topical medications and missed applications of test cream were recorded at each visit.

Light Microscopy

A 2 mm punch biopsy was taken pre- and post-treatment from a PIH lesion on the face or arm and from normal facial skin. Where feasible a PIH lesion of sufficient size was selected and pre- and post-treatment biopsies were obtained from the same lesion carefully avoiding scar tissue from the pretreatment biopsy. In some patients, due to the small size of the PIH lesions as well as to avoid scar tissue from the pretreatment biopsy, the post-treatment biopsy was taken from a different but nearby PIH lesion.

Specimens were fixed in 10% neutral-buffered formalin, and processed for routine hematoxylin and eosin staining. The histological sections were examined by one dermatopathologist (L.J.F.) who was not involved in the clinical part of the study and was unaware of the group to which the patient was assigned and which specimens were pre- or post-therapy. The following parameters were evaluated on a scale of zero to four (0=absence and 4=maximum)—stratum corneum compaction, granular cell layer thickness, spongiosis, epidermal and dermal melanin. Epidermal thickness (from the top of the granular layer to the basement membrane zone) in µm was measured in 5 high power fields (HPF). Mitotic figures and melanocyte numbers were counted in 5 HPF and the mean values used.

Statistical Methods

Changes in clinical and histological parameters of PIH lesions and normal skin from pretherapy to week 40 were compared between RA- and vehicle-treated groups using a two-sample t-test. The association between treatment and overall response at week 40 was made with the Chi-Square test. Color changes of PIH lesions in RA- and vehicle-treated groups, assessed by both clinical observation and colorimeter, were compared using the average value of the four designated lesions. In addition, the same comparison was made for normal skin using the designated normal site on the face. In each case, the group means were analyzed using the two-sample t-test. The strength of the relation between clinically discernable color change and color change detected by the colorimeter was assessed with Pearson's product-moment correlation coefficient.

All p values are two-sided. Summary statistics are expressed as means ±1 S.E.M. Data were analyzed with the Michigan Interactive Data Analysis System (MIDAS, a statistical software package developed by the Statistical Research Laboratory at the University of Michigan).

Photography

At baseline, weeks 12, 24 and 40 of treatment, color photographs for documentation of PIH lesions were taken by a professional photographer. Standardized positioning and broad, diffuse illumination using two studio flash units were used for all patients. A Kodak gray card (18% reflectance) was included in the first frame of each patient's photographic session to control for extrinsic variables. All film was of the same emulsion lot and was processed by the same professional laboratory.

RESULTS

Of 68 patients enrolled, 14 withdrew prior to completion of the study. Eleven patients withdrew due to noncompliance, not attending scheduled visits (6 in the RA and 5 in the vehicle-treated group), two (both in the RA-treated group) had an exacerbation of eczema and one patient in the RA-treated group experienced a retinoid reaction after two weeks of therapy. The withdrawals were not related to the usage of the experimental cream except in patients who withdrew due to exacerbation of eczema and from retinoid reaction. Therefore, clinical data are presented for 54 subjects (30 in the vehicle-treated group and 24 in the RA-treated group). The major causes of PIH by clinical diagnosis in the subjects enrolled were acne (62 patients), folliculitis (3), eczema (5), ingrown facial hairs (4) and shaving irritation (10). Fifteen patients had more than one clinical diagnosis as the cause of PIH.

Overall

Figure 2:
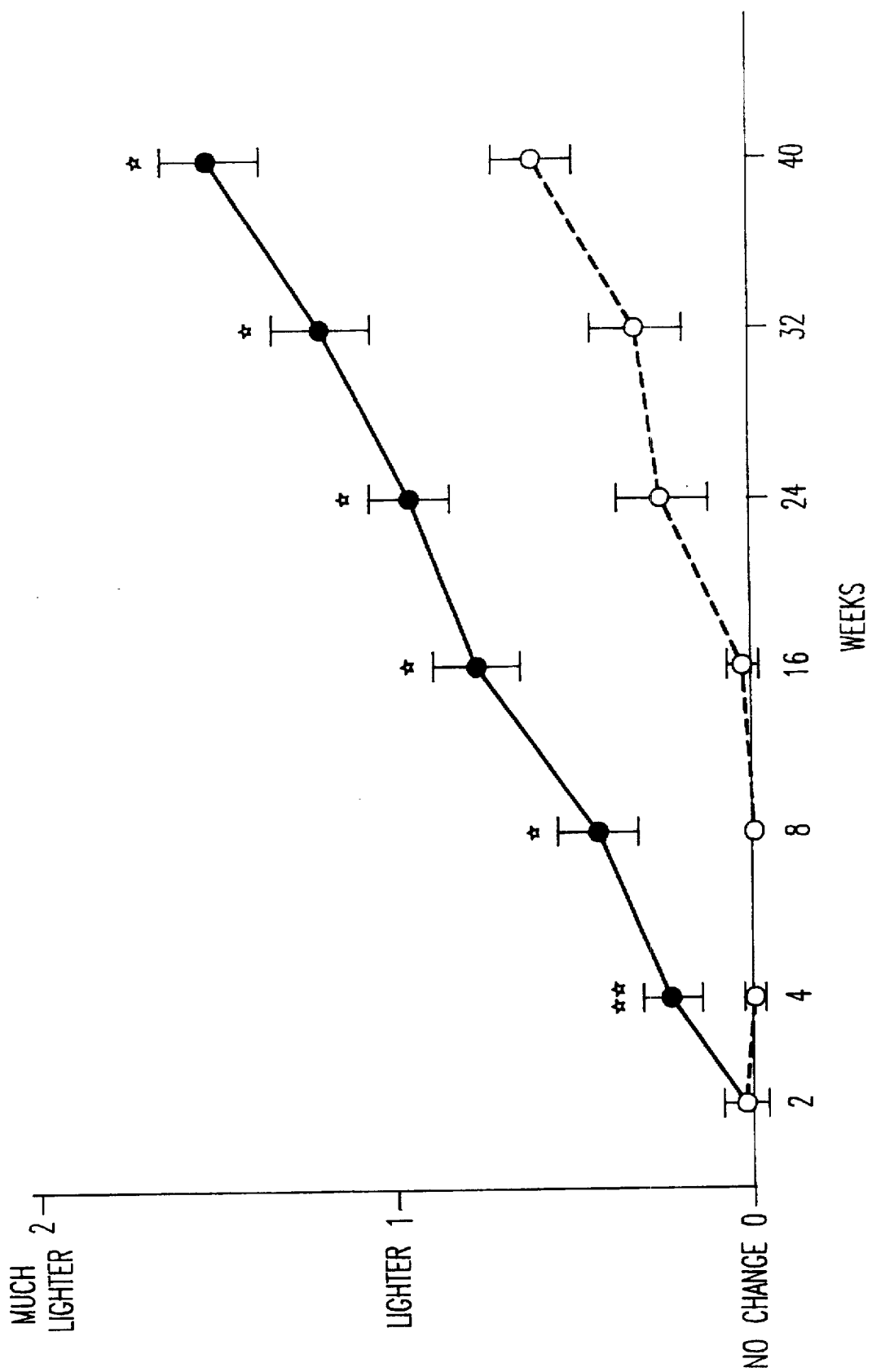
FIG. 2 graphically illustrates the overall color change of facial post-inflammatory hyperpigmentation as a result of treatment with 0.1% RA cream (solid line) or vehicle (broken line). VAlues are means ±SEM. Statistically significant and clinically detectable lightening of lesions was present as early as 4 weeks after initiation of therapy with 0.1% RA (**, $p=0.009$). This improvement was maintained for all subsequent time points (*, $p \leq 0.0002$). At and beyond 16 weeks the lightening of vehcile-treated lesions is probably due to spontaneous resolution thereby delineating the natural history of this form of pigmentation.

Overall evaluation of the RA-treated group after 40 weeks, demonstrated clinically significant improvement as compared to the vehicle-treated group (see FIG. 1, $P<0.0001$). In 14 of 24 (58%) of the RA-treated patients, facial lesions were evaluated as much lighter, in 8 (33%) as lighter and in 2 (8%) the same when compared to pretherapy. In contrast, in vehicle-treated patients, PIH lesions on the face were scored as much lighter in 2 of 30 subjects (7%) of subjects, lighter in 15 of 30 (50%) and unchanged from pretherapy in 13 (43%) (see FIG. 1). Neither group had patients evaluated as worse or much worse. Since only 7 patients had PIH lesions on the arms, overall scores for arms were not included. The time from initiation of RA therapy to when overall lightening of PIH lesions was first achieved was week 4 (see FIG. 2, $P=0.009$). This clinical improvement was maintained throughout the study when compared to the vehicle group.

Individual PIH lesions: Significant clinical lightening (mean color change from baseline) of RA- versus vehicle-treated PIH lesions was observed after 40 weeks of therapy (2.6±0.2 vs 1.9±0.2, respectively; $P=0.03$).

Figure 3A:
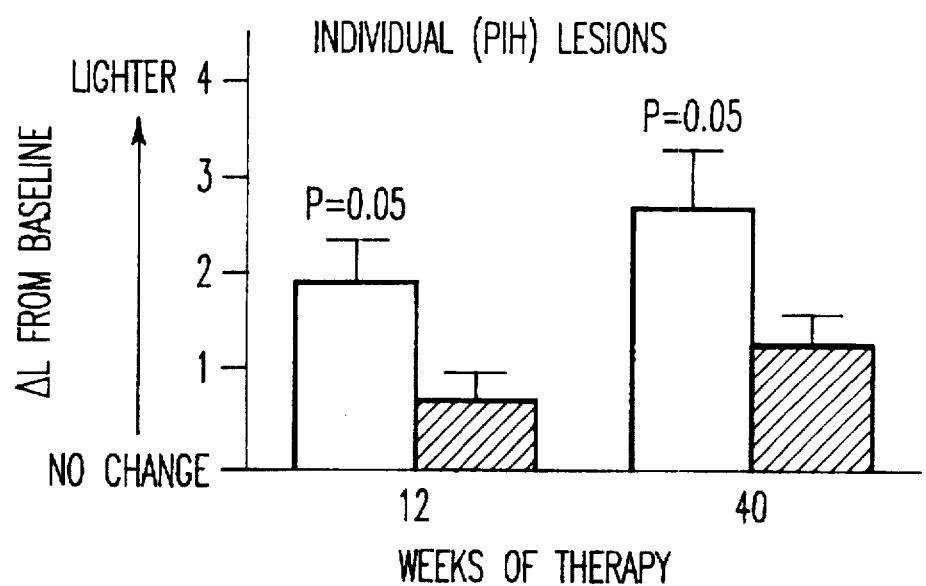
FIG. 3 graphically presents the colorimeter measurement of color change in individual lesions of post-inflammatory hyperpigmentation (PIH) and normal skin in response to treatment with 0.1% RA cream (open bars) or vehicle (solid bars). An increase in the L or reflectance value by colorimeter indicates a lightening in skin color. Values are means ±S.E.M. By 12 weeks of treatment with 0.1% RA cream there is significant lightening of pigmented lesions as compared with vehicle treatment ($p=0.05$). This RA-induced lightening is continued to 40 weeks ($p=0.05$) Normal skin treated with 0.1% RA cream lightens as compared with baseline whilst normal skin treated with vehicle darkens over the 40 week treatment period ($p=0.0001$), this lightening takes place slowly with no statistically significant difference between RA and vehicle at the 12 week time period.
Figure 3B:
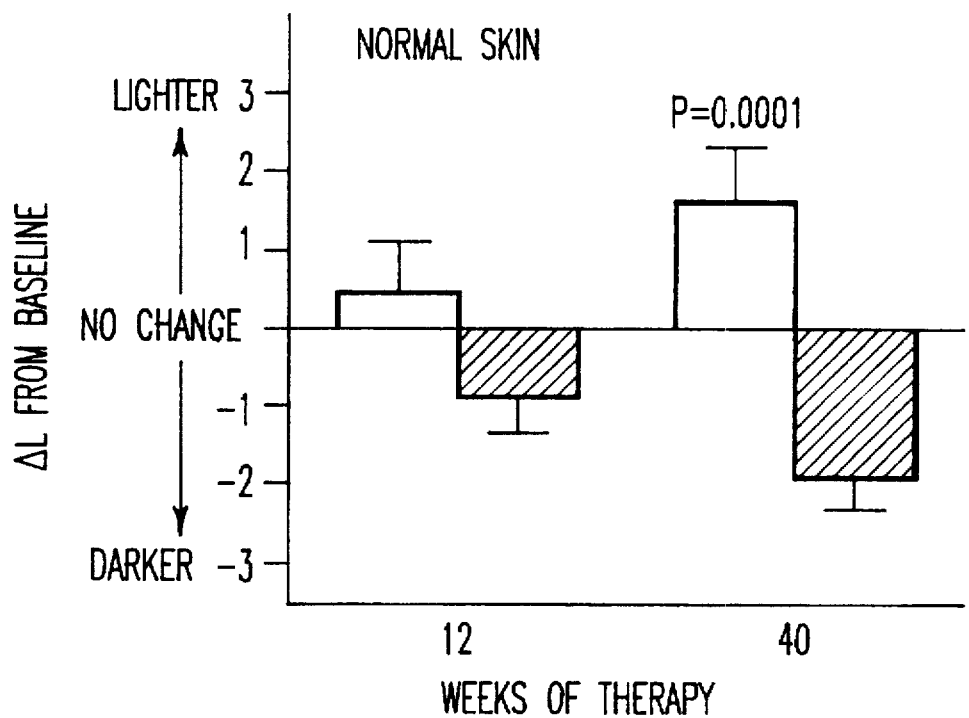

The colorimeter demonstrated an increase in the lightening scale of 2.7±0.7 in PIH lesions treated with RA for 40 weeks compared to an increase of 1.2±0.4 in vehicle-treated lesions ($p=0.05$, FIG. 3). Since the average pretherapy L (reflectance) value for PIH lesions was 40.6±0.6 and the corresponding average for normal skin was 47.3±0.6, it can be said that 40 weeks of treatment with RA produced a 40 Percent lightening of PIH lesions from their original color toward a normal skin tone compared to an 18% lightening of vehicle treated lesions. The change in color detected by the colorimeter from baseline to week 40 was significantly correlated with the clinically discernable color change of the 4 individual PIH lesions ($r=0.43$, $p=0.001$)

Normal Skin: The difference in mean color change (clinical lightening) between the RA and vehicle group although statistically significant, $p=0.055$ (using a conservative 2-tailed test), was subtle and barely discernible clinically.

Lightening of RA treated normal skin was also detected by the colorimeter with an average lightening of 1.6±0.7 compared to a darkening in the vehicle group of 1.9±0.4 ($p=0.0001$, FIG. 3). Since there is no defined endpoint for lightening of normal skin, it was not possible to quantify the change in terms of percent lightening as we did for PIH lesions.

Histology

Normal skin: Topical RA produced statistically significant increases in stratum corneum compaction, granular layer thickness, epidermal thickness, mitotic figures and spongiosis (increased inter-keratinocyte spaces) as compared to vehicle (Table I). After 40 weeks a statistically insignificant ($p=0.07$) 11% decrease in epidermal melanin was detectable in the RA treated group in comparison with a 22% increase in the vehicle treated group. In RA-treated patients a marginally significant ($p=0.06$) 40% increase in dermal melanin was observed in comparison with a 1% decrease in the vehicle group (Table I).

PIH lesions: Treatment for 40 weeks with topical RA produced statistically significant increases in stratum corneum compaction, granular layer thickness and spongiosis as compared to vehicle (Table II). In RA-treated patients an insignificant ($p=0.24f$) 28% decrease in epidermal melanin was observed in comparison with a 3% decrease in the vehicle group (Table II). In RA-treated patients an insignificant ($p=0.14$) 49% increase in dermal melanin was observed in comparison with a 7% decrease in the vehicle group (Table II).

TABLE I

NORMAL BLACK SKIN: HISTOLOGY RESULTS AFTER 40 WEEKS OF TOPICAL RA 0.1% VS. VEHICLE THERAPY

| | RETINOIC ACID (0.1%) n = 24 | | | VEHICLE n = 28 | | | |
|---|---|---|---|---|---|---|---|
| | Pre-therapy | Post-therapy | % Change | Pre-therapy | Post-therapy | % Change | P value** |
| Epidermal Thickness (μm) | 55 ± 3 | 69 ± 5 | ↑26 | 58 ± 3 | 50 ± 2 | ↓13 | 0.002 |
| Epidermal Melanin | 1.9 ± 0.2 | 1.6 ± 0.2 | ↓11 | 1.6 ± 0.1 | 1.9 ± 0.2 | ↑22 | 0.07 |
| Spongiosis | 1.0 ± 0.2 | 1.9 ± 0.2 | ↑93 | 1.0 ± 0.2 | 0.7 ± 0.1 | ↓27 | 0.001 |
| Granular Cell Layer | 0.8 ± 0.1 | 2.2 ± 0.2 | ↑169 | 0.8 ± 0.1 | 0.9 ± 0.1 | ↑4 | <0.0001 |
| Stratum Corneum Compaction | 1.3 ± 0.3 | 2.4 ± 0.2 | ↑83 | 1.2 ± 0.2 | 1.0 ± 0.2 | ↓21 | 0.0003 |
| Dermal Melanin | 1.1 ± 0.2 | 1.5 ± 0.2 | ↑40 | 1.4 ± 0.2 | 1.3 ± 0.2 | ↓1 | 0.060 |
| Dermal Inflammation | 1.4 ± 0.1 | 1.2 ± 0.2 | ↓12 | 1.3 ± 0.1 | 1.2 ± 0.1 | ↓7 | 0.74 |
| Melanocyte Number 5/HPF | 25 ± 2 | 27 ± 1 | ↑9 | 21 ± 1 | 24 ± 1 | ↑18 | 0.48 |
| Mitotic Figures 5/HPF | 0.2 ± 0.1 | 0.5 ± 0.1 | ↑225 | 0.5 ± 0.1 | 0.3 ± 0.1 | ↓36 | 0.019 |

All measurements represent mean ± SEM and except for epidermal thickness and numbers of mitotic figures and melanocytes are based on a semi-quantitative 0–4 scale where 0 = none and 4 = maximum. Percentages were determined before rounding of the means.
*For each patient specimen, measurements from top of granular layer to epidermal basement membrane at 5 inter-rete sites were averaged.
**Represents significance of change from before treatment in the RA versus vehicle groups.

TABLE II

PIH IN BLACK SKIN: HISTOLOGY RESULTS AFTER 40 WEEKS OF TOPICAL RA 0.1% VS. VEHICLE THERAPY

| | RETINOIC ACID (0.1%) n = 24 | | | VEHICLE n = 28 | | | |
|---|---|---|---|---|---|---|---|
| | Pre-therapy | Post-therapy | % Change | Pre-therapy | Post-therapy | % Change | P value** |
| Epidermal Thickness (μm) | 76 ± 6 | 82 ± 5 | ↑7 | 71 ± 4 | 62 ± 2 | ↓13 | 0.077 |
| Epidermal Melanin | 2.2 ± 0.2 | 1.7 ± 0.3 | ↓23 | 2.4 ± 0.2 | 2.3 ± 0.2 | ↓3 | 0.024 |
| Spongiosis | 1.0 ± 0.2 | 1.9 ± 0.2 | ↑84 | 1.2 ± 0.2 | 0.9 ± 0.1 | ↓23 | 0.004 |
| Granular Cell Layer | 1.2 ± 0.2 | 2.8 ± 0.2 | ↑141 | 1.1 ± 0.2 | 1.5 ± 0.2 | ↑39 | 0.001 |
| Stratum Corneum Compaction | 1.7 ± 0.3 | 2.8 ± 0.2 | ↑69 | 1.7 ± 0.2 | 1.7 ± 0.2 | ↓4 | 0.008 |
| Dermal Melanin | 0.9 ± 0.2 | 1.4 ± 0.2 | ↑49 | 1.6 ± 0.2 | 1.5 ± 0.2 | ↓7 | 0.14 |
| Dermal Inflammation | 1.6 ± 0.2 | 1.9 ± 0.2 | ↑17 | 2.1 ± 0.2 | 1.6 ± 0.2 | ↓24 | 0.067 |
| Melanocyte Number 5/HPF | 24 ± 1 | 27 ± 1 | ↑13 | 25 ± 1 | 26 ± 1 | ↑2 | 0.17 |
| Mitotic Figures 5/HPF | 0.5 ± 0.2 | 0.7 ± 0.2 | ↑42 | 0.4 ± 0.1 | 0.3 ± 0.1 | ↓30 | 0.23 |

All measurements represent mean ± SEM and except for epidermal thickness and numbers of mitotic figures and melanocytes are based on a semi-quantitative 0–4 scale where 0 = none and 4 = maximum. Percentages were determined before rounding of the means.
*For each patient specimen, measurements from top of granular layer to epidermal basement membrane at 5 inter-rete sites were averaged.
**Represents significance of change from before treatment in the RA versus vehicle groups.

Short Term Safety

Adverse reactions from use of the RA were limited to minimal to moderate retinoid reaction. A score of 2 or more for erythema or desquamation (on a 0–4 scale where 0 =none, 4=severe) at 2 or more visits constituted a retinoid reaction and was observed in 13 of 24 (53%) patients receiving RA and none of vehicle-treated patients. The retinoid reaction was present only in areas that came into contact with active medication. There was a tendency to gradual diminution in severity, frequency and duration of reactions as the study progressed. Cutaneous reactions were well tolerated and apart from 3 subjects did not prevent continued participation in the study. The reactions improved in response to application of emollients or by temporarily reducing or discontinuing the test cream for one to three days. Of note, no subject on RA therapy manifested hyperpigmentation nor gross depigmentation as a side effect.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for treating hyperpigmentation of black skin, comprising administering to a patient in need thereof an effective amount of a pharmaceutical composition consisting essentially of retinoic acid.

2. The method of claim 1, wherein said administering is topical application to the skin.

3. The method of claim 1, wherein said retinoic acid is administered in an amount of 0.5 to 10 mg/cm$^2$ of the skin treated.

4. The method of claim 1, wherein said hyperpigmentation is post-inflammatory hyperpigmentation.

5. The method of claim 1, wherein said pharmaceutical composition is in the form of an oil, ointment, cream, lotion, or gel.

6. The method of claim 1, wherein said pharmaceutical composition further consists essentially of an ingredient selected from the group consisting of water, oils, alcohols, emulsifying agents, perfumes, coloring agents, fillers, abrasive agents, and moisturizers.

7. A method of lightening black skin, comprising treating said skin with an effective amount of a pharmaceutical composition consisting essentially of retinoic acid.

8. The method of claim 7, wherein said administering is topical application to the skin.

9. The method of claim 7, wherein said retinoic acid is administered in an amount of 0.5 to 10 mg/cm$^2$ of the skin treated.

10. The method of claim 7, wherein said pharmaceutical composition is in the form of an oil, ointment, cream, lotion, or gel.

11. The method of claim 7, wherein said pharmaceutical composition further consists essentially of an ingredient selected from the group consisting of water, oils, alcohols, emulsifying agents, perfumes, coloring agents, fillers, abrasive agents, and moisturizers.

* * * * *